(12) United States Patent  
Tuli

(10) Patent No.: US 10,928,344 B2  
(45) Date of Patent: Feb. 23, 2021

(54) SLOTTED SENSOR FOR DETECTION OF MOISTURE IN A DIAPER

(71) Applicant: Raja Singh Tuli, Montreal (CA)

(72) Inventor: Raja Singh Tuli, Montreal (CA)

(*) Notice: Subject to any disclaimer, the term of this patent is extended or adjusted under 35 U.S.C. 154(b) by 0 days.

(21) Appl. No.: 15/818,136

(22) Filed: Nov. 20, 2017

(65) Prior Publication Data

US 2019/0154607 A1    May 23, 2019

(51) Int. Cl.
| | |
|---|---|
| *G01R 31/00* | (2006.01) |
| *G01N 27/07* | (2006.01) |
| *A61F 13/42* | (2006.01) |
| *G01N 33/493* | (2006.01) |

(52) U.S. Cl.
CPC ............. *G01N 27/07* (2013.01); *A61F 13/42* (2013.01); *A61F 2013/424* (2013.01); *G01N 33/493* (2013.01)

(58) Field of Classification Search
USPC .............................. 324/71.1, 76.11, 600, 691
See application file for complete search history.

(56) References Cited

U.S. PATENT DOCUMENTS

| | | |
|---|---|---|
| 4,106,001 A | 8/1978 | Mahoney |
| 5,838,240 A | 11/1998 | Johnson |
| 6,559,772 B2 | 5/2003 | Zand et al. |
| 7,737,322 B2 * | 6/2010 | Ales, III ................ A61F 13/42 604/361 |
| 8,884,769 B2 | 11/2014 | Novak |
| 9,291,589 B2 | 3/2016 | Wong et al. |
| 2011/0319845 A1 | 12/2011 | Kuo et al. |
| 2014/0200538 A1 * | 7/2014 | Euliano ................... A61F 13/42 604/361 |
| 2017/0016845 A1 * | 1/2017 | Lee ..................... G01N 27/3272 |
| 2019/0070043 A1 * | 3/2019 | Collette .................. A61F 13/42 |

* cited by examiner

*Primary Examiner* — Vincent Q Nguyen

(57) ABSTRACT

A system for sensing wetness in an ordinary diaper includes a disposable sensor unit which has a sensor strip and support structure. The sensor strip has electrical circuit with conductive elements as wetness sensors printed on the bottom surface of the strip, wherein a closed electrical circuit is formed when an amount of body fluid is present that subsequently triggers an alerting device. The support structure has multiple slots cut out on it to expose conductive elements to urine and also keeps the conductive elements at a specific height from the diaper's padding such that urine content retained by a soaked diaper do not raise alarms.

23 Claims, 11 Drawing Sheets

SLOTTED SENSOR FOR DETECTION OF MOISTURE IN A DIAPER

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND

Field of the Invention

This invention relates to devices for monitoring wetness, particularly in diapers, wherein a sensor unit is fastened to an absorbent layer of any ordinary diaper such that absorbent layer of the ordinary diaper does not touch sensory elements of the sensor unit.

Description of Related Art

For many years, a variety of designs have been developed for detecting and signalling the presence of urine in a diaper. However, most of these designs require manufacturing modifications to ordinary diapers in order to be implemented. For instance, a pouch like insert inside the diaper is required to house an alerting device as disclosed in U.S. Pat. No. 8,884,769. The '769 patent describes a moisture sensor having conductive leads placed at different position within the moisture sensor to identify the location of urine. However, the conductive leads are placed on top of an absorbent layer and hence, even with a small amount of moisture that is retained by the absorbent layer upon absorption of the urine, the conductive leads will continue to detect moisture. This happens as the conductive leads remain in contact with the absorbent layer with retained moisture. This results in false detection of urine in the diaper, when the diaper has already absorbed the urine.

In U.S. application Ser. No. 13/064,832, moisture is sensed using electrodes that are placed in between layers of a diaper and thus cannot be used in ordinary diapers. A similar way of embedding the urine sensing electrodes in between different layers of a diaper is disclosed in U.S. Pat. No. 9,291,589.

In some other cases, a detection strip is placed on an absorbent layer of a garment, like U.S. Pat. No. 4,106,001. The '001 patent disclose a clip-on garment device with a detection strip having two electrodes running lengthwise along the strip, that is used to generate an alert when a garment has become wet. However, the detection strip is placed in contact with the garment and hence, even with a small amount of moisture that is retained by the garment upon absorption of urine, the detection strip will continue to detect moisture. This happens as the detection strip remains in contact with the garment always. In case of diapers, the absorbent layer is an absorbent material that can hold large quantity of urine before it needs to be replaced. Hence, using the detection strip of the '001 patent in a diaper would result in a continuous alarm from the time urine is excreted.

Further, the wetness sensor and the alerting device are configured as non-detachable in some prior art systems, wherein the entire device must be discarded when the wetness sensor becomes worn. Thus, such alerting devices become relatively expensive to manufacture.

U.S. Pat. No. 5,838,240 discloses a wetness sensing strip and alerting system that are detachable from each other with the alerting device being adhesively bonded to the outside surface of a diaper. However, the sensing strip carries a pair of spaced conductors that are placed on a top permeable layer of the diaper. And thus, could not eliminate the problem of detecting absorbed moisture present on the top permeable layer of the diaper.

Adult females do have a higher tendency of excreting small amount of urine from time to time, which gets absorbed by the absorbent layer of a diaper. Existing moisture sensors would continue to detect moisture retained by the top permeable layer even after the urine gets absorbed, as sensing elements in the existing moisture sensor remains in contact with the absorbent layer of the diaper. This might result in generation of false alarms. Hence, there is a necessity to identify moisture sensor that can be placed on top of an absorbent layer of an ordinary diaper to detect urine, such that the moisture sensor does not detect moisture retained by a top permeable layer of the diaper after the urine is absorbed.

BRIEF SUMMARY OF THE INVENTION

The invention described herein depicts a moisture sensing and alerting system comprising an alerting device and a sensor unit. It is intended that the present invention is used on an ordinary diaper that needs no structural modification. One objective of the present invention is to provide a sensor unit having a sensor strip that can be attached to any ordinary diaper, wherein the sensor strip has no direct contact with any layer of the diaper. In yet another objective of the present invention is to provide a method of detecting urine in an ordinary diaper without generating false alarms by detecting moisture retained by a top permeable layer of the diaper after the urine has been absorbed.

According to an aspect of the present invention, the sensor strip is made up of plastic or similar hydrophobic materials and has electrodes printed on its bottom surface that faces top permeable layer of a diaper. The top permeable layer of the diaper is the layer that faces a wearer and can be called as a wearer side of the diaper also. The electrodes run through the entire length of the sensor strip and the sensor strip is long enough to be attached to a diaper such that sensor strip as per the present invention covers a detection area from the groin to the hip of a wearer. The electrodes can be used to measure multiple electrical parameters including, but not limited to, resistance, capacitance, conductivity, impedance etc. By monitoring the various electrical parameters through the electrodes printed on the sensor strip, the degree and/or locations of wetness of the diaper that is caused by urine or other body fluid is detected. A support structure made up of foam rubber or similar insulating materials is attached to the bottom surface of the sensor strip and slots are made in places to expose the electrodes through the slots. The support structure holds the sensor strip at an elevation from the top permeable layer of the diaper, such that even when the top permeable layer of the diaper is retaining a portion of moisture from absorbed urine, the top permeable layer does not touch the electrodes and thus the retained moisture does not cause generation of false alarms. A temporary yet resilient electrical connection is established between the sensor strip and the alerting device such that the moisture sensed by the sensor strip is processed by the alerting device to provide an alert signal or the like by wireless means or wired means. The alerting device can be attached to the diaper using any known-in-the-art mechanisms such that the alerting device gets electrically coupled with the sensor strips. The sensor strip is designed to be disposable with the absorbed diaper while the alerting device can be ready for immediate reuse by uncoupling it from the sensor strip.

In another embodiment, plurality of small pores are created in the sensor strip, not overlapping the electrodes, to allow body fluid on top of the sensor strip to pass on to the diaper through the support structure.

In another embodiment, the thickness of the support structure is slightly more in a central region compared to edge regions so as to create a small bulge in the sensor strip at a central region of the sensor strip. Thus, the small bulge at the central portion of the sensor strip allows urine to slide sideways to the top permeable layer of the diaper.

In another embodiment, the sensor unit can be used to detect number of times a wearer has excreted and also the location and the amount of urine that has been excreted.

BRIEF DESCRIPTION OF THE DRAWINGS

The various preferred embodiments of the present invention described herein can be better understood by those skilled in the art when the following detailed description is read with reference to the accompanying drawings. The components in the figures are not necessarily drawn to scale and any reference numeral identifying an element in one drawing will represent the same element throughout the drawings.

The figures of the drawing are briefly described as follows.

DETAILED DESCRIPTION OF THE INVENTION

The invention described herein is designed to work along with an absorbent article like an ordinary diaper, for people having medical problems such as bladder incontinence or for babies. The present invention discloses a moisture detecting and alerting system comprising a disposable moisture sensor unit having multiple sensing elements and a portable alerting device, preferably of non-disposable type, electrically coupled to the sensing elements. One aspect of the present invention is to identify volume of urine excreted by a wearer of a diaper using the sensing elements. The moisture detecting and alerting system can also be used to identify the saturation level of the diaper. Another purpose of the present invention is to provide a method to attach the disposable moisture sensor unit to any ordinary diaper without requiring any structural alteration, wherein the sensing elements present on the disposable moisture sensor strip has no contact with an absorbent layer of the diaper. The sensing elements can detect moisture when body fluid is excreted by a wearer of the diaper and the alerting device connected to the sensing elements can generate alerts basis the moisture sensed by the sensing elements. The sensor unit is attached on top of a top permeable layer of the diaper such that the sensing elements does not detect moisture retained by the top permeable layer of the diaper after the diaper has absorbed the bodily fluid excreted by a wearer. Thus, the alerting device does not generate an alert when the body fluid is absorbed by the diaper. The sensing elements as per the invention can also be used to detect number of times a wearer has excreted, before the diaper needs to be changed. The sensing elements as per the invention can also be used to identify the amount of urine excreted by a wearer.

Figure 1A:
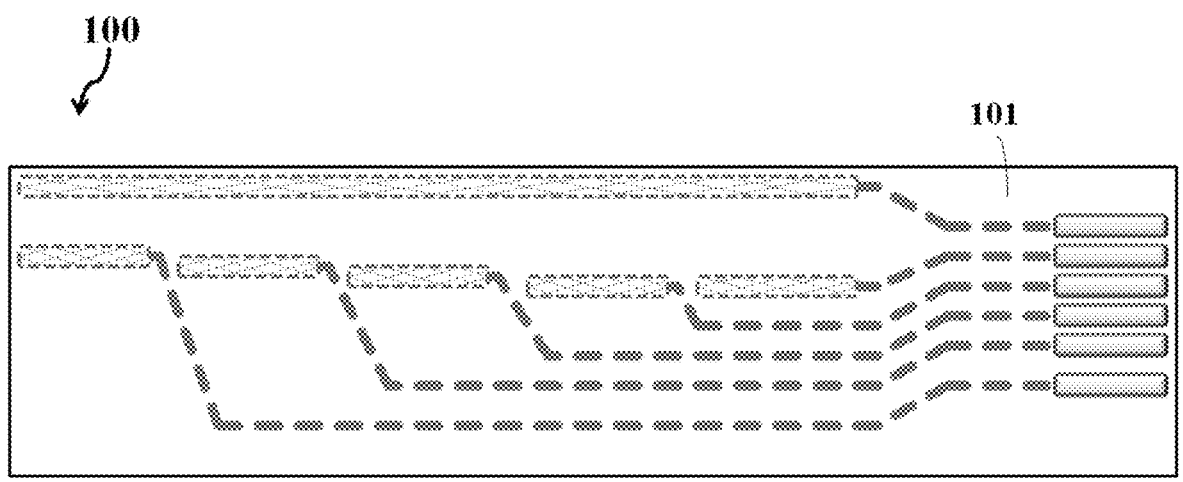
FIG. 1A is a plan view of top surface of a sensor strip of the present invention.
Figure 1B:
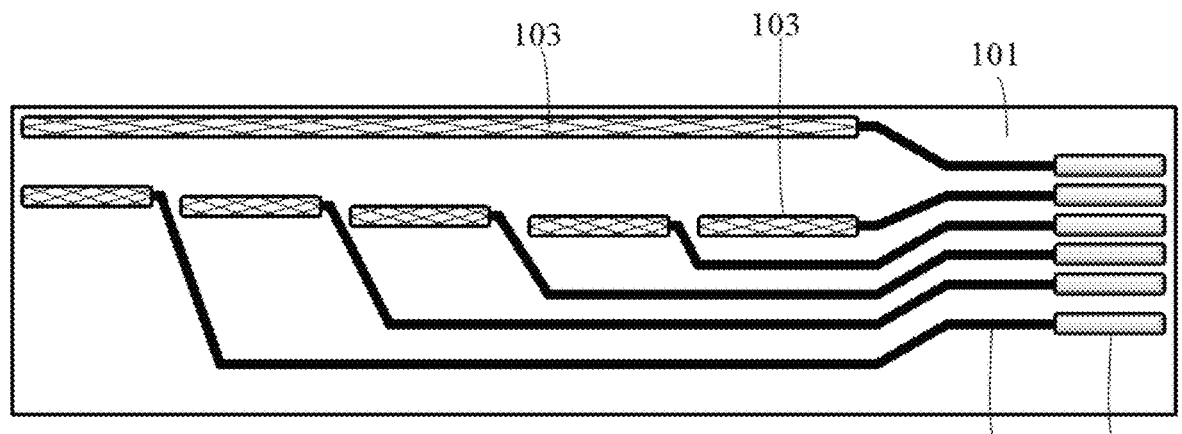
FIG. 1B is a plan view of bottom surface of the sensor strip of the present invention without a plastic insulating layer.
Figure 1C:
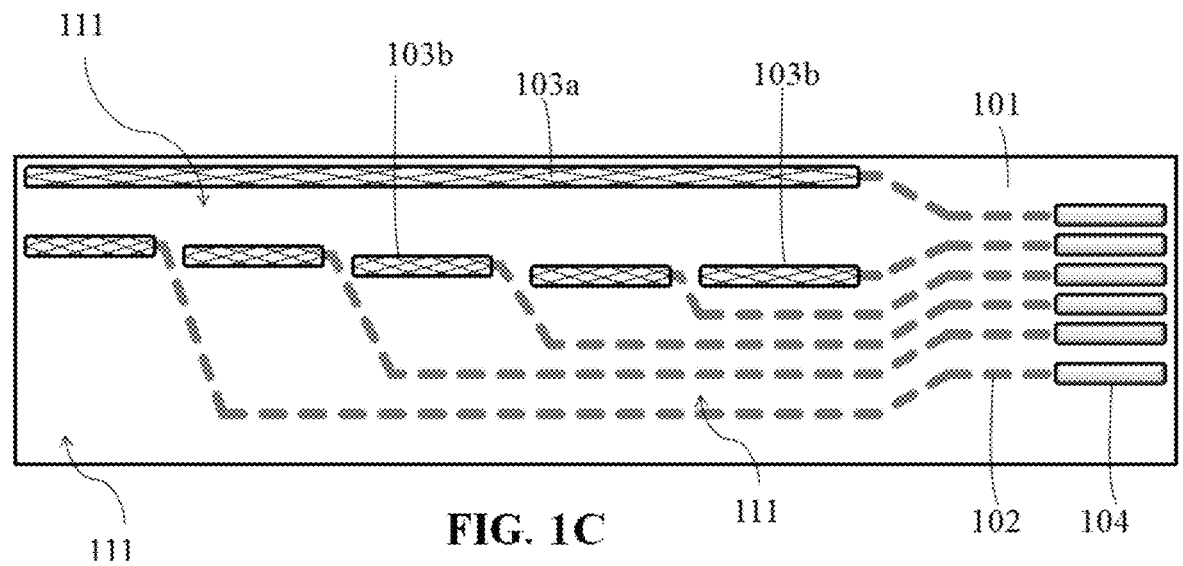
FIG. 1C is a plan view of the bottom surface of the sensor strip with a plastic insulating layer.

FIG. 1A-1C illustrate plan views of a disposable sensor strip 101, as per one of the embodiment of the present invention. The sensor strip 101 made up of flexible elongated piece of low cost hydrophobic material, preferably plastic so as to be used only once and be disposed with a soaked diaper. On bottom surface of the sensor strip 101 as illustrated in FIG. 1B, there is an electrical circuit comprising of multiple elongated, spaced apart and relatively parallel conductive bands 102 printed in conductive carbon ink or similar types of conducting inks. At the rear end of each of the conductive bands 102 are sensing elements or electrodes 103 that act as moisture sensors, which may also be printed in conductive carbon ink or similar types of conducting inks. The electrodes 103 can be of any design as intended. However, as per the preferred embodiment of the present invention, the electrodes 103, comprises of two parallel electrodes 103a and 103b. Any one of the electrodes 103a or 103b can be a single unit whereas the other can be designed as composed of discreet electrode sections so as to identify location of moisture. As per the preferred embodiment of the invention, electrode 103a is a single electrode whereas the electrode 103b comprises of discreet electrode sections. The multiple electrodes 103 are distributed along the longitudinal direction of the sensor strip 101. The front end of each of the conductive bands 102 is terminated with contact terminals 104, which may be made up of silver foil or other conductive materials, to facilitate making an electrical connection with an external alerting device so that moisture detected by the electrodes 103 in the sensor strip 101 can be further analysed. Further, as shown in FIG. 1C, a plastic insulating layer 111 is printed bottom surface of the sensor strip 101, on the top of the conductive bands 102, such that the plastic insulating layer covers the entire bottom surface of the sensor strip 101 without covering the electrodes 103 and the contact terminals 104. Thus, only the electrodes 103 are exposed to detect moisture at various locations. The plastic insulating layer 111 is very thin layer of plastic coating and can be printed using multiple methods known to a person ordinary skilled in the art, including silk-screening.

The size, pattern and location of the electrodes 103 shown in FIG. 1A-1C are merely one non-limiting example while alternatives are also conceivable to a person skilled in the art. Further, design and position of the conductive bands 102 and the electrodes 103 are adjusted according to variations in diaper size.

Figure 2A:
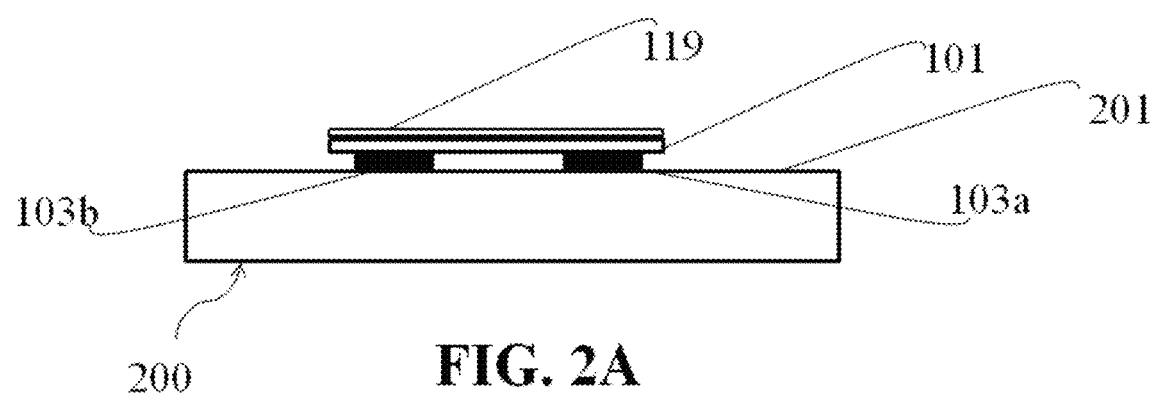
FIG. 2A is a cross-sectional view of the sensor strip affixed to a ordinary diaper.

FIG. 2A illustrates a cross sectional view of the disposable moisture sensor strip 101 placed on top of an inner surface of an ordinary diaper 200, as per one of the embodiment of the present invention. The sensor strip 101 is placed in such a way that the electrodes 103a and 103b face a top permeable layer 201 of the ordinary diaper 200. The top permeable layer 201 of the diaper 200 is the layer that faces a wearer and can also be called as a wearer side of the diaper 200. As shown in the FIG. 2A, the electrodes 103a and 103b touch the top permeable layer 201 of the ordinary diaper 200.

Figure 2B:
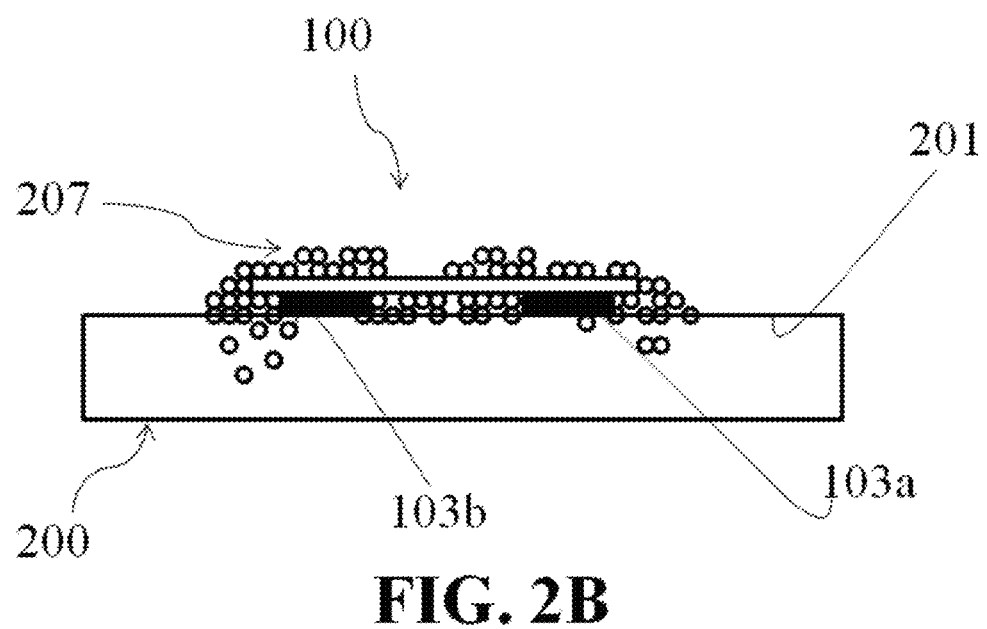
FIG. 2B is a cross-sectional view of the sensor strip affixed to a diaper when body fluid is excreted inside the diaper.
Figure 2C:
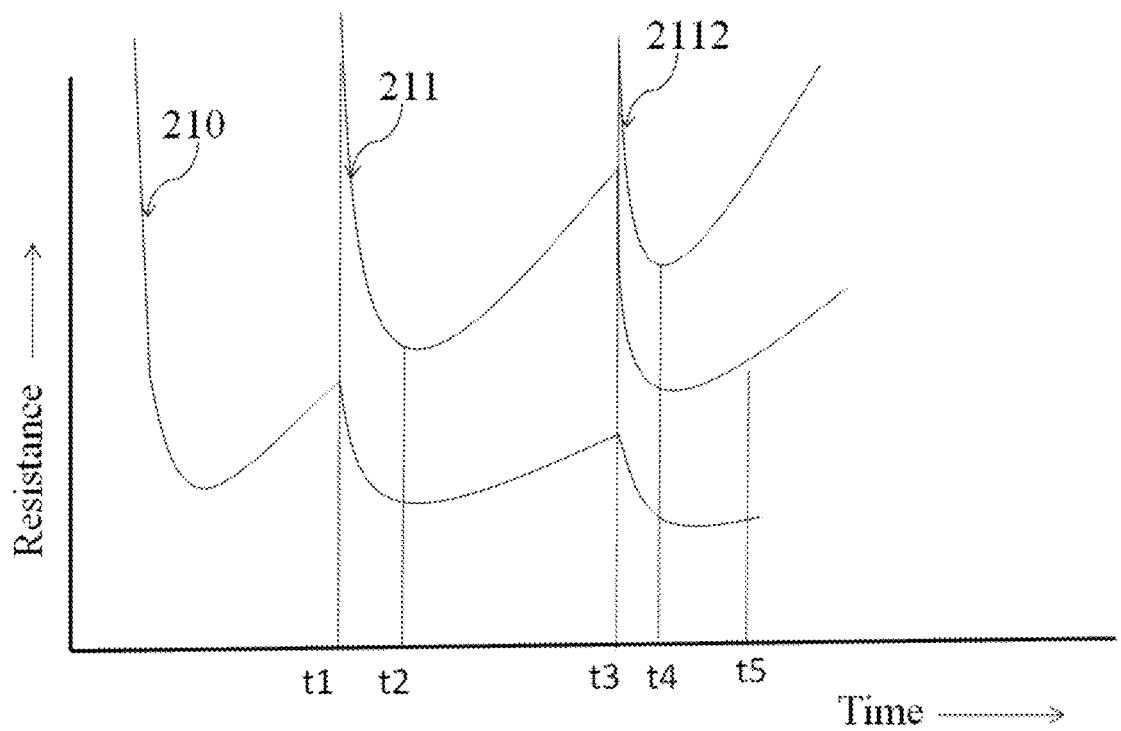
FIG. 2C is a graphical representation of resistance detected by an alerting device between two electrodes when a user urinates inside the diaper over a course of time.

Sometimes, a sheet of non-woven fabric 119 can be placed on top of the sensor trip 101, so as to increase comfort of the wearer. When a wearer urinates inside the diaper 200, urine 207 forms a closed circuit between the electrodes 103a and 103b, as shown in FIG. 2B. An alerting device, electrically coupled to the electrodes can detect the closed circuit formed between the electrodes 103a and 103b. When the diaper 200 is not wet, there is no closed circuit between the electrodes 103a and 103b and hence, resistance between them can be considered as extremely high. With the formation of a closed circuit, the resistance between the electrodes 103a and 103b will decrease. When the urine 207 starts to get absorbed inside the diaper 200, the resistance between the electrodes 103a and 103b starts to rise again. However, since the top permeable layer 201 of the ordinary diaper 200 retains some amount of absorbed urine as moisture, a closed circuit still remains between the electrodes 103a and 103b, but with comparatively high resistance. When urine is discharged again, the resistance of the closed circuit between the electrodes 103a and 103b decreases again and when, the urine gets absorbed inside, the resistance of the closed circuit between the electrodes 103a and 103b rises again. The process is repeated whenever urine is excreted inside the diaper 200 till the time the diaper 200 gets saturated and could not absorb in more urine. An alerting device, coupled to the electrodes 103a and 103b, can detect the formation of the closed circuit between the electrodes 103a and 103b and can track the change of resistance of the closed circuit that happens every time a wearer urinates. This change of resistance is illustrated by a graph trace 210 shown in FIG. 2C. Also, when the wearer urinates multiple times, the urine starts to spread over the top permeable layer 201 of the ordinary diaper 200, touching the electrodes 103a and 103b at new locations. Thus, with more and more urine, more closed circuits are formed between electrode 103a and different sections of electrode 103b, which are present on different locations. Thus, each new closed circuit that is formed represent present of urine at a new location in the diaper 200. For example, as shown in FIG. 2C, when the wearer starts to urinate again at time t1, urine spreads across the diaper to form a new closed circuit between and electrode 103a and another section of electrode 103b. The resistance of the new closed circuit is shown in FIG. 2C by graph trace 211. With more and more urine, other closed circuits are formed between electrode 103a and different sections of electrode 103b. Resistance of one such other closed circuit is shown using graph trace 212. To estimate saturation level of the ordinary diaper 200 using the sensor strip 101, multiple factors are considered. One such factor is to detect the rise and fall of resistance in the closed circuits that are formed. When the wearer urinates, the resistance of a closed circuit formed between any one sections of electrode 103b and electrode 103a, falls to a low level within a very short amount of time. As shown in FIG. 2C, when the wearer starts to urinate again at time t1, resistance of the closed circuit starts to reduce to a lower level. When the wearer stops urinating at time t2, the resistance starts to increase as the urine starts getting absorbed inside the diaper 200. Such an event, between time t1 and t2, when resistance of a closed circuit falls steeply, can be called as an urination event. After an urination event, when the urine starts getting absorbed inside the diaper 200, the resistance starts rising over a period of time. With subsequent urination events, portion of the top permeable layer 201 between the section of electrode 103b and electrode 103a starts to get saturated and hence, could only absorb small amount of urine. Thus, resistance depicted by graph trace 210 starts to reach a minimum value. After another urination event, from time t3 to t4, urine in between this section of the electrode 103b and electrode 103a will get absorbed inside the diaper 200 in minimal amount. Hence, rate of rise of resistance, depicted by graph trace 210, over a period of time t5, after the wearer stops urinating at time t4, will be very low. To calculate saturation level of this portion of the diaper 200, a percentage threshold is assigned to the rate of rise of resistance after an urination event. When the rate of rise of resistance of a closed circuit is less than a percentage threshold over a defined period of time t5, after an urination event, then that portion of the diaper 200 can be considered as saturated. Also, it must be noted that small changes in resistance might occur because the wearer of the diaper 200 is moving. Such small changes in resistance might be tracked by noticing the resistance levels of the small changes and be eliminated from the process of saturation level calculation as noise. As mentioned earlier, with subsequent urination, new closed circuits are formed, resistance of which are also tracked and are depicted using graph traces 211 and 212. Also, each of these new closed circuits that are formed represents presence of urine between electrode 103a and different sections of electrode 103b, which are spread across different portions of the diaper 200. Also, when a user urinates, the urine can spread across the diaper 200 and will cause new closed circuits between electrode 103a and different sections of electrode 103b. Those new closed circuits will also have a steep fall in resistance. The steep fall in resistances in the new closed circuits does not necessarily indicate that a user has started urinating, but indicates that the urine has spread across to new locations. Even then, such a steep drop in resistances is considered as an urination event for the new closed circuits. Each of the graph trace 211 and 212 can be used to identify saturation level of their respective portions of the diaper 200. Hence, if the highest resistance of any of the closed circuits depicted using graph trace 212 and 211 is around a percentage threshold of the resistance of an already saturated closed circuit 210, then it can be ascertained that the respective portion of the diaper 200 is also saturated. For example, resistance of the closed circuit depicted by graph trace 211 may be 80% of resistance of the closed circuit depicted by graph trace 210, whereas resistance of another closed circuit depicted by graph trace 212 may be 60% of resistance of the closed circuit depicted by graph trace 210. Thus, it can be ascertained that amount of urine present in the portion of the diaper 200 under the closed circuit depicted by graph trace 211 is different from amount of urine present in portion of the diaper 200 under the closed circuit depicted by graph trace 212. Hence, saturation level of different portions of the diaper 200 can be ascertained using resistance of the corresponding closed circuit and comparing it to resistance of a saturated closed circuit. A threshold can be assigned while comparing resistances to determine saturation level, so that when resistance of a closed circuit is at least a predefined threshold percentage of resistance of a saturated closed circuit, corresponding area of the diaper under the closed circuit can be considered as saturated. The predefined threshold percentage can vary based upon location of closed circuit as well as type of the diaper, processing algorithm used in the detecting device etc. In another aspect of the present invention, the predefined threshold percentage can also be calculated dynamically. Hence, saturation level of the diaper 200 can be ascertained using any one or combination of factors, including (a) resistance of at least one of the closed circuits formed is at a minimum value, (b) rise of the resistance of the at least one of the closed circuits, after an urination event, over a period of time t5 is less than a threshold, (c) multiple closed circuits, other than a saturated closed circuit, are formed and (d) total added resistances of the multiple closed circuits that are formed is at least a predefined threshold percentage of resistance of a saturated closed circuit. Taking into consideration all this factors, saturation level of the diaper 200 can be determined.

Figure 2D:
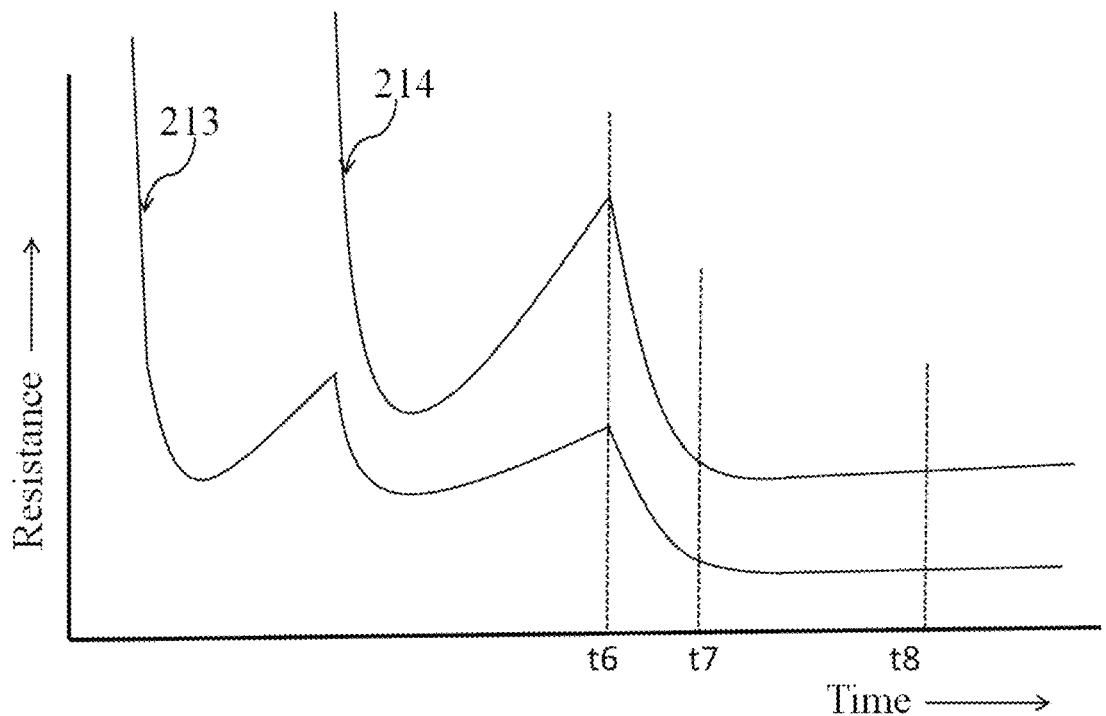

FIG. 2D represents resistances of closed circuits in the diaper 200 when it is saturated. As shown in FIG. 2D, only two closed circuits can be formed, if not more and yet, the diaper can be considered as saturated based on percentage increase of resistance of the two closed circuits after an urination event. Graph trace 213 and 214 represents resistances of the two closed circuits formed as per this embodiment of the present invention. After an urination event, from time t6 to t7, the resistance of the closed circuit represented by 213 increase very slowly over a period of time. The rise of resistance is monitored for a predetermined time, t8. If after the predetermined time t8, the increase of the resistance of the closed circuit represented by 213 is less than x %, than corresponding portion of the diaper 200 can be considered as saturated. The x % can vary based upon the type of diaper and location of electrode, and is generally around 1%. The predetermined time t8 can be y minutes, wherein the y minutes can vary between 10 minutes to 20 minutes, and is preferably kept around 15 minutes. Similarly, if resistance of the closed circuit represented by 214, also increases to less than x % over the predetermined time t8 after an urination event, than corresponding portion of the diaper 200 can also be considered as saturated. Since, at least two closed circuits are formed and resistance of the at least two closed circuits rise to less than x % over a predetermined time, entire diaper 200 can be considered as saturated.

As per another embodiment of the present invention, the diaper 200 can be considered as saturated, if at least one closed circuit is determined to be saturated and at least three closed circuits are formed between electrode 103a and three adjacent sections of electrode 103b. However, to determine saturation level using above method requires tracking of resistances for a long duration of time. In many cases, resistances of the closed circuits rise back too slowly, and that further increases the time required to determine saturation level of a diaper. Using a support structure underneath the sensor strip 101, the rise of resistance can be tracked more quickly as described in below embodiments.

Figure 3A:
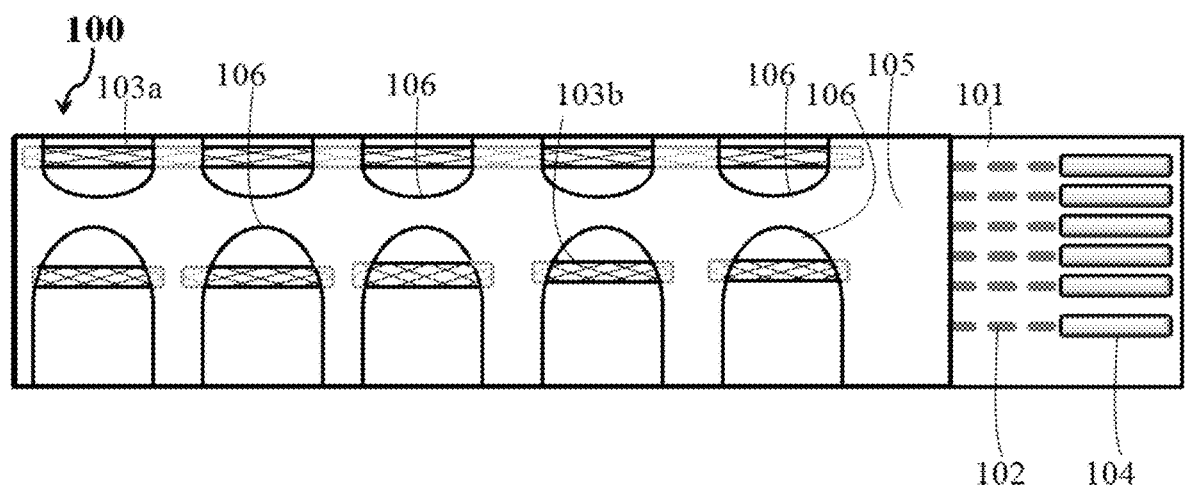
FIG. 3A is a plan view of the bottom surface of the sensor strip with a support structure in the principal embodiment of the present invention.

FIG. 3A shows the bottom surface of the sensor strip 101 along with a support structure 105, attached to the sensor strip 101 below the electrodes 103a and 103b, as per the primary embodiment of the present invention. The sensor strip 101, the support structure 105 and an alerting device all comprises a moisture sensor unit 100 as per the primary embodiment of the present invention. The support structure 105 has slots 106 cut out from it to expose electrodes 103 at multiple places. The support structure 105 can be attached to the sensor strip 101 using known in the art glues or similar adhesive substances. The support structure 105 is made up of foam rubber or sponge or similar materials that can act as an insulator. It should be noted that the material of the support structure 105 be chosen such that it does not alter absorption factors of the ordinary diaper. At predetermined places on the back side of the support structure 105 are a peel-and-stick backing with non-conductive double-sided adhesive units (not shown), which are covered by a protective films prior to use. When in use, the protective films are peeled off such that the sensor unit 100 can be adhesively bonded to a diaper.

Figure 3B:
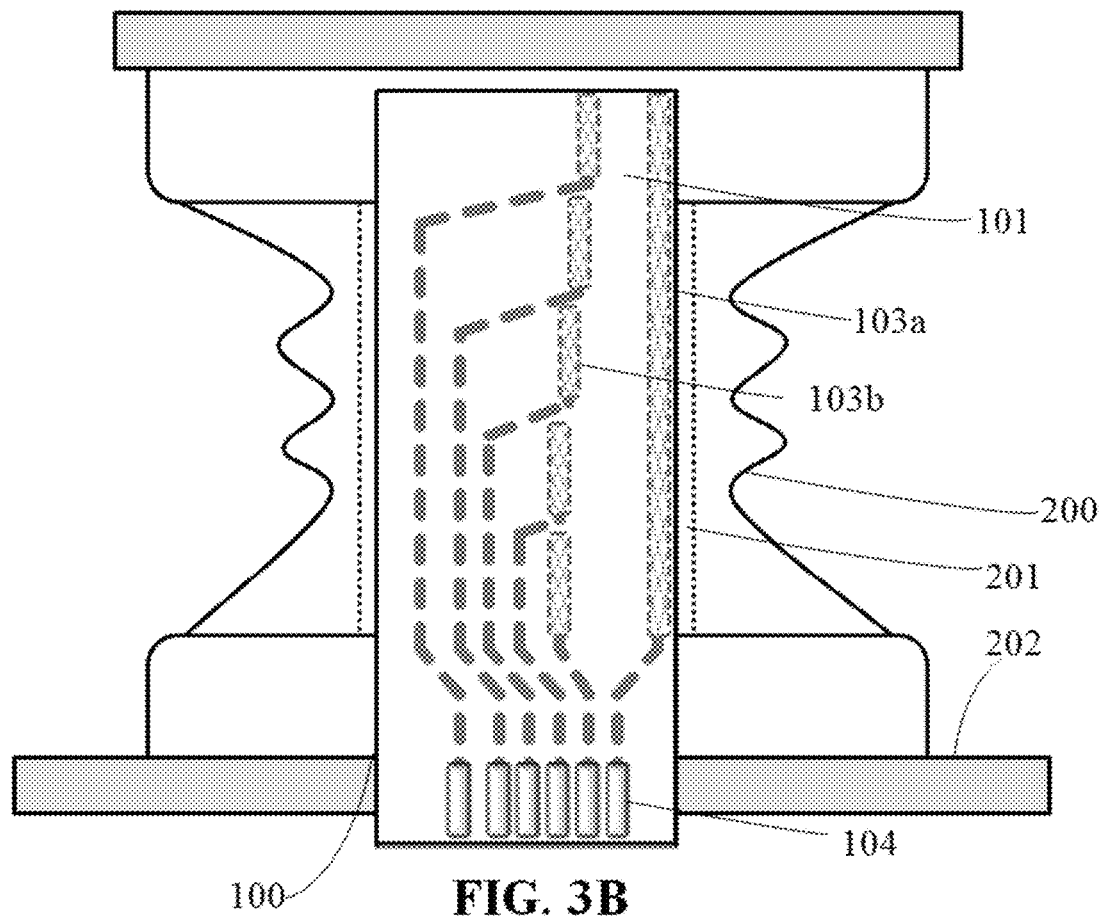
FIG. 3B is a plan view of the sensor strip affixed to a diaper in the principal embodiment along with the support structure.

In accordance with the primary embodiment of the present invention, as shown in FIG. 3B the moisture sensor unit 100 along with the supports structure 105, can be used with an ordinary diaper 200 that needs no further structural modification. The sensor unit 100 is adhered to the center of the top permeable layer 201 of a diaper 200 by the double-sided adhesive units on the support structure 105, such that the electrodes 103a and 103b, present on the bottom surface of a sensor strip 101, face the top permeable layer 201 of the diaper 200. When a sensor unit 100 in matching length and size with the diaper 200 is used, the electrodes 103a and 103b on the sensor strip 101 will cover a detection area from the front portion to the rear portion of the diaper 200, corresponding to the region from the groin to the hip of a human body, respectively. In one of the embodiment, a certain length of the sensor strip 101 protrudes out of the diaper's front waistband 202 and is intended to be sufficiently long enough for an alerting device to be wrapped in the sensor strip 101 with a minimum of one complete rotation and half rotation of the alerting device. In alternative embodiments, the sensor strip 101 is long enough to reach the front waistband 202 of the diaper upon which an alerting device can be clamped or attached to the diaper 200, such that the contact terminals 104 of the sensor strip 101 are electrically coupled with the alerting device. Further, the sensor strip 101 is designed not to affect the absorbency of the diaper 200.

Figure 3C:
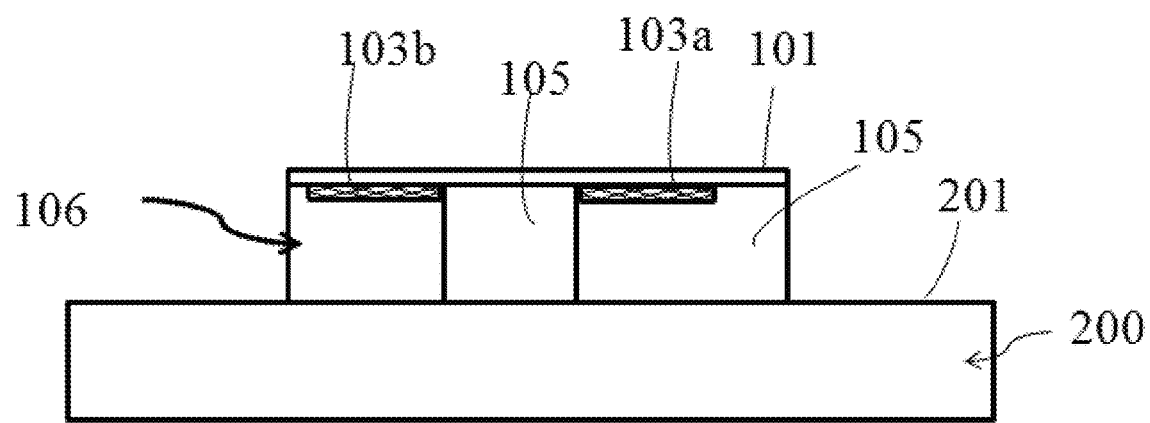
FIG. 3C is a cross-sectional view of the sensor strip affixed to a diaper along with the support structure in the principal embodiment.

In FIG. 3C, a cross section of one of the sensor unit 100 when attached to the diaper 200 as per one of the embodiment of the invention is shown. A support structure 105 is attached on the bottom surface of the sensor strip 101 below the electrodes 103. Slots 106 are cut out from the support structure 105 in places overlapping the electrodes 103a and 103b, so that the electrodes 103a and 103b are exposed towards the top permeable layer 201, through the slots 106. The support structure 105 is made up of insulating material such as foam rubber, sponge or similar insulating materials that can be attached to the back side of the sensor strip 101 using glues or other known in the art adhesive mechanisms. The thickness of the support structure 105 is such that it can be used to create a gap between the electrodes 103 of the sensor strip 101 and the top permeable layer 201 of the diaper 200. Capillary action (sometimes called capillarity, capillary motion, or wicking) is the ability of a fluid to flow in narrow spaces without the assistance of, or even in opposition to, external forces like gravity. Hence, the gap is created at places of the slots 106 and is large enough to prevent capillary action of urine or similar body fluids. The thickness of the support structure 105 as well as the dimension of the slot should be selected in such a way that the urine or similar body fluids is prevented from getting stuck in between the electrodes 103 and the top permeable layer 201 of the diaper 200. The thickness of the support structure 105 is kept preferably between 1 mm to 2 mm to attain the desired functionality, as per one of the embodiment of the invention. In case, the gaps created by the slots 106 and the thickness of the support structure 105 is narrow, urine or similar body fluids can get stuck inside the gaps due to capillary action and as a result may cause false sensing of moisture. Hence, the thickness of the support structure 105 and the dimension of slots 106 should be chosen carefully to avoid such phenomenon. As it can be conceivable to a person skilled in the art that thickness of the support structure 105 is relative to the sensor strip 101 and the electrodes 103a and 103b, and can be altered easily so as to prevent capillary action of urine in the gap between the electrodes 103a and 103b, and the top permeable layer 201 of the diaper 200.

Figure 4:
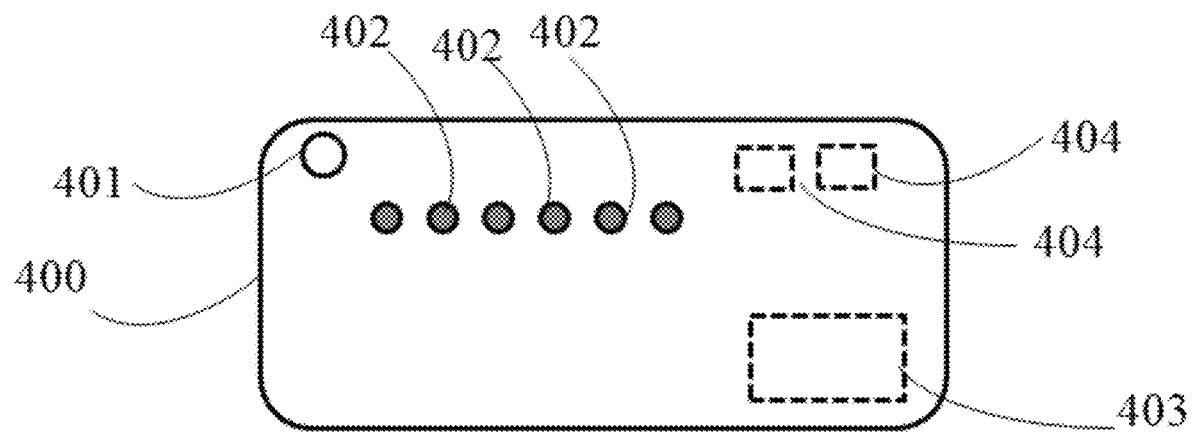
FIG. 4 is a plan view of the alerting device in the principal embodiment.

Referring to FIG. 4 now, a portable alerting device 400 made up of insulating material is shown. The alerting device 400 has contact points 402 which are used to connect to contact terminals 104 of the sensor strip 101. The contact points 402 is made up of conducting materials as they couple the sensor unit 100 to processing components 404 present inside the alerting device 400. The alerting device 400 is adapted to receive and process moisture detection signals picked up through the electrodes 103 of the sensor strip 101 and subsequently, analyse the processed signals to provide an alert or the like by wireless or wired means. For example, the alert may include sending a text message to a caretaker's cell phone with information about the degree of wetness and the location(s) of wetness on a diaper. The alerting device 400 is also capable of generating a visible or an audible alert signal through its inbuilt indicators 401. In that case, the alert may also be a visual or an audible alert generated by in-built indicators 401, indicating the amount of body fluid excreted and when the diaper needs to be changed. The battery 403 present in the portable alerting unit 300, provides electric power to the processing components 404, as well as supplies power to the electrodes 103 on the sensor strip 101. The portable alerting device 400 is designed to be attached to the sensor unit 100 using multiple techniques including clamping or adhesive or mechanical based fastening products or snap lid or by wrapping around the sensor strip or other similar mechanisms.

Figure 5A:
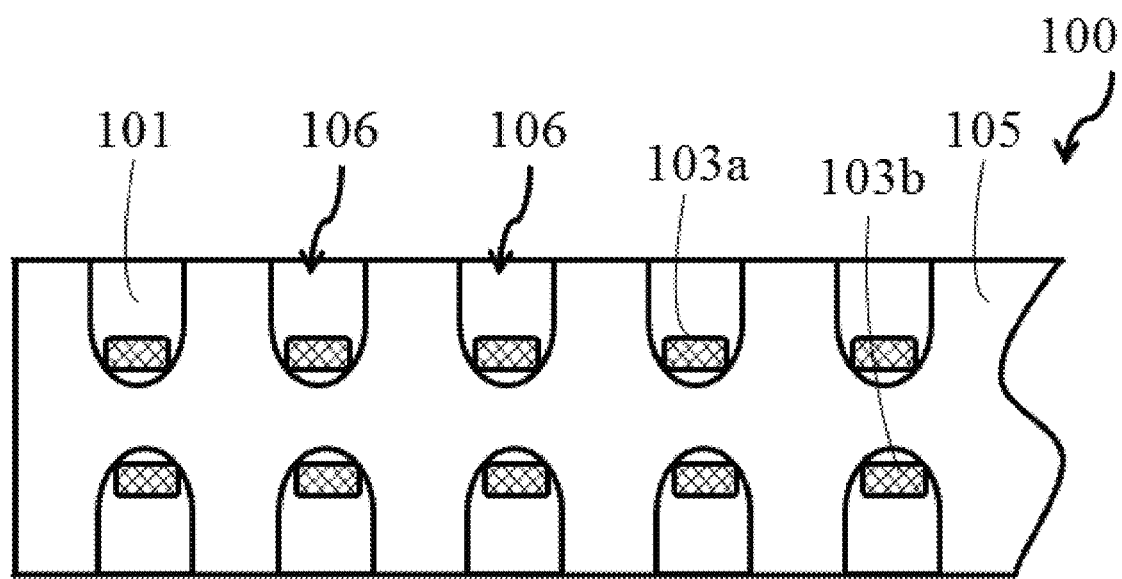
FIG. 5A is the plan views of the bottom surface of the sensor strip with discrete set of electrodes.

In accordance with yet another embodiment of the invention, as shown in FIG. 5A, both of the electrodes 103a and 103b are not continuous and the slots 106 are provided on the support structure 105 in places where the electrodes 103 are present. The electrodes 103a and 103b are present throughout the entire length of the sensor strip 101 and so does the slots 106. As per the primary embodiment of the invention, the number of slots 106 and the number of electrodes 103a and 103b are same. The slots 106 are cut out on the support structure 105 to expose the electrodes 103a and 103b at predetermined locations that act as zones for detecting body fluids such as urine. The shape of the slots shown in this figure is an exemplary one and not intended to limit the scope of the invention. As per another embodiment of the invention, having more slots than the electrodes is also possible and can be used in case of having a single continuous electrodes running through the length of the sensor strip 101, such that slots can be used to expose the single continuous electrode at multiple places to detect urine at the multiple places. Further, the dimension of the electrodes can be made such that a slot can completely expose its corresponding electrode or an electrode section. In yet another embodiment of the present invention, slots are usually made smaller than the dimension of the electrodes such that a slot can partially expose its corresponding electrode.

Figure 5B:
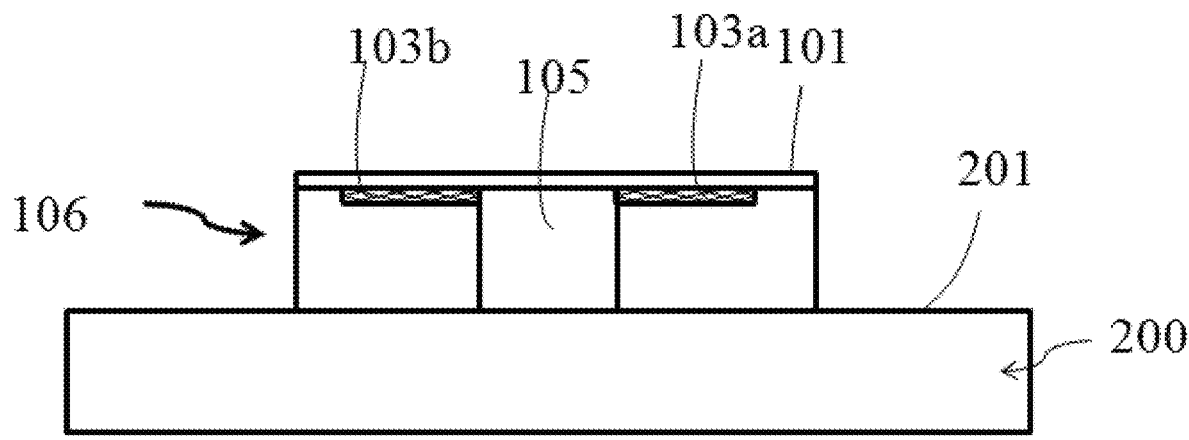
FIG. 5B is a cross sectional view of the sensor strip with discreet set of electrodes when placed on a diaper as per one of the embodiment.

In FIG. 5B, a cross section of one of a sensor unit 100 as per one of the embodiment of the present invention is shown. The support structure 105, with slots 106 cut out in it, is attached on the bottom surface of the sensor strip 101, below the electrodes 103a and 103b. The slots 106 are cut out in such a way that the slots 106 overlap the electrodes 103a and 103b at multiple places. Preferably, the thickness of the adhesive units (not shown) is kept as small as possible so that there remains no gap between the supports structure 105 and the absorbent layer 201 of the diaper 200, when the sensor unit 100 is attached to the diaper 200. As mentioned in the earlier embodiments, the thickness of the support structure 105 is chosen in such a way that it can be used to create a non-capillary gap between the electrodes 103a and 103b of the sensor strip 101 and the absorbent layer 201 of a diaper at the places of the slots 106. Also, the support structure 105 and the sensor strip 101 should be bonded tightly with each other so that there is no space in between the sensor strip 101 and the support structure 105.

Figure 6A:
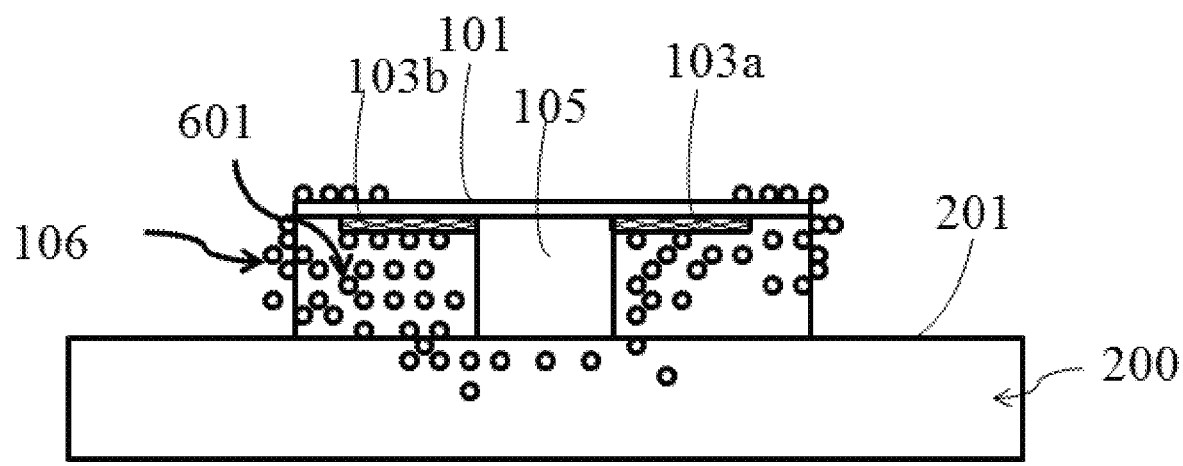
FIG. 6A is a cross sectional view of the sensor strip along with the support structure when placed on a diaper when body fluid is excreted as per one of the embodiment, wherein the body fluid is not travelling through the support structure.
Figure 6B:
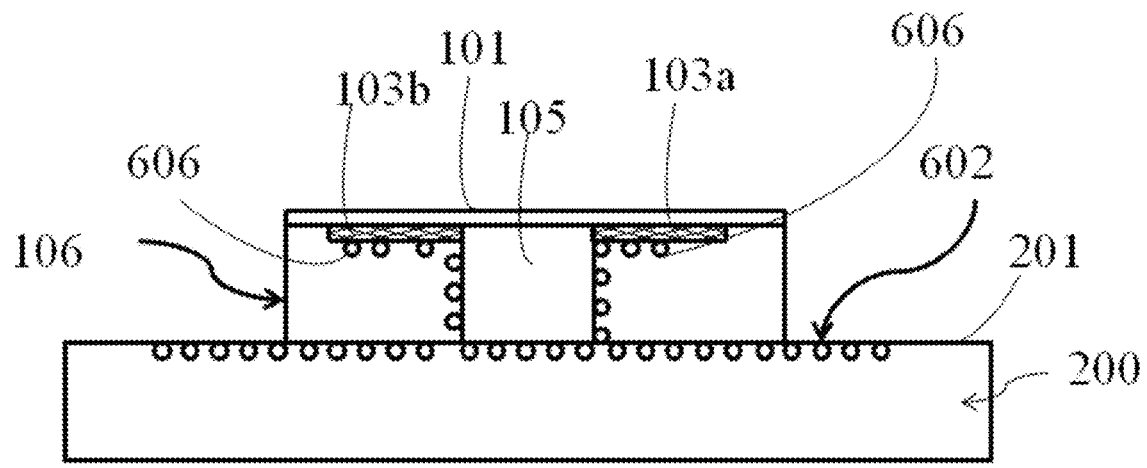
FIG. 6B is a cross sectional view of the sensor strip along with the support structure when placed on a diaper when the body fluid is absorbed by the diaper as per one of the embodiment.

As shown in FIG. 6A-6B, when body fluid, such as urine 601 is excreted, the urine traverses from the top surface of the sensor strip 101 into the top permeable layer 201 of the diaper 200. From the top permeable layer 201, the urine 601 traverses to internal absorbent layers of the diaper 200. Thus, when the urine 601, which contains not only water but also dissolved salts and ions that acts as electrolytes, is not fully absorbed by the diaper 200, it forms a closed circuit between the electrodes 103a and 103b, as shown in FIG. 6A and thus an alert is generated by the alerting device 400. The alerting device 400 continues to generate the alert as long as the electrodes 103a and 103b remain in electrical connection to each other via the urine 601. When the urine 601 is absorbed by the diaper 200, the closed circuit substantially breaks contact and alerting device cease to generate the alert. However, as shown in FIG. 6B, sometimes small amount of urine 606 may remain in contact with surfaces of the electrodes 103a and 103b, and the support structure 105. Thus, the closed circuit formed will still remain, but the resistance of the closed circuit will be very high compared to earlier. Thus, the closed circuit between the electrodes 103a and 103b can be considered as substantially an open circuit because of its high resistance, when the urine 601 is absorbed in the diaper 200. Even when the top permeable layer 201 absorbs the urine 601 to pass on to the internal absorbent layers of the diaper 200, the top permeable layer 201 retains a relatively small amount of the urine as moisture 602, as shown in FIG. 6B. As a result of the gap, created by the slots 106, between the electrodes 103a and 103b and the top permeable layer 201 of the diaper 200, the moisture 602 retained by the absorbent layer 201 does not cause a closed circuit between the two electrodes 103a and 103b. Thus, the moisture 602 is not sensed by the electrodes 103a and 103b and as a result the alerting device 400 does not generate an alert for the retained moisture present on the top permeable layer 201. When a wearer of the diaper 200 urinates again, the electrodes 103a and 103b will again get electrically connected to each other through the urine and thus, a detection process of the urine will start again. Since the electrodes 103a and 103b provide detection areas at various locations along the longitudinal direction of the diaper 200, the wetness locations can then be identified based on the locations of current flow in the urine bridged closed circuit. In further embodiment of the present invention, the duration of the alert generated can be an indicator of the amount of urine excreted by the wearer. If the duration of the alert is continuous, then it can be considered that the diaper is completely soiled and cannot absorb urine any more. In a further embodiment, other electrical circuitry may be implemented to measure the capacitance or voltage change of the wetted diaper such that the degree of wetness of the diaper can be evaluated. Therefore, the present invention allows identification of the wetness location along a diaper as well as the degree of wetness at each of the detection areas.

Figure 6C:
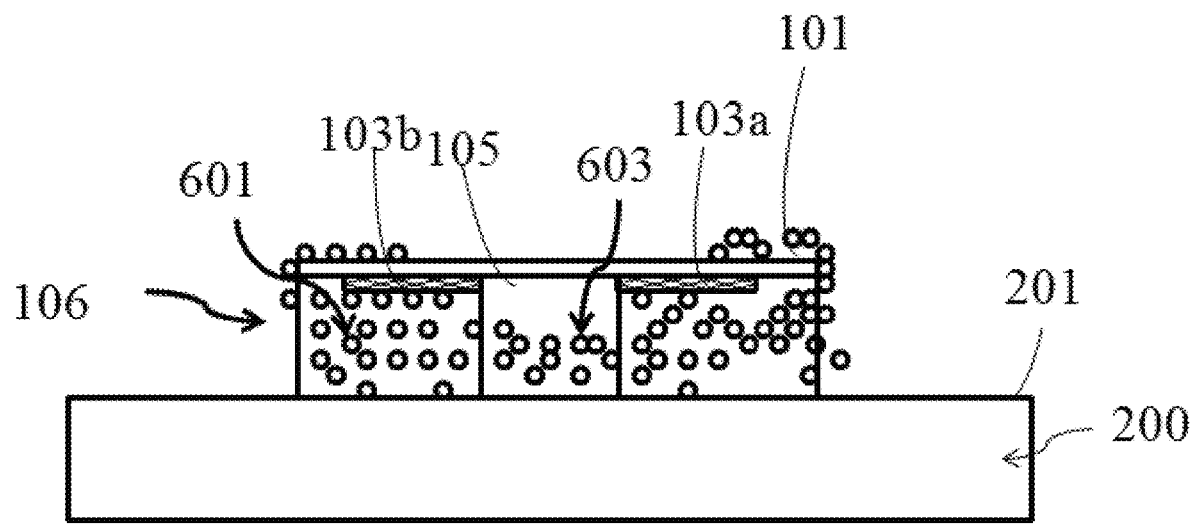
FIG. 6C is a cross sectional view of a sensor strip along with the support structure when placed on a diaper when body fluid is excreted as per one of the embodiment, wherein the body fluid is travelling through the support structure.
Figure 6D:
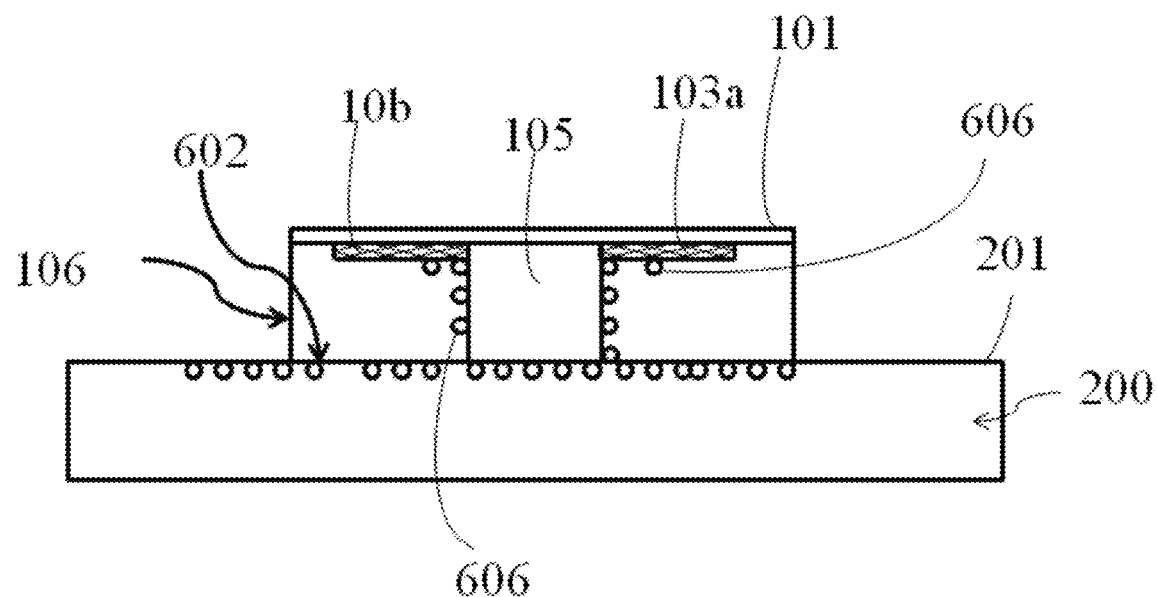
FIG. 6D is a cross sectional view of a sensor strip along with the support structure when placed on a diaper when the body fluid is absorbed by the diaper as per one of the embodiment, where the body fluid in the support structure is also absorbed by the diaper.

In yet another aspect of the invention, as shown in FIG. 6C-6D, a portion 603 of the body fluid, such as urine 601 is absorbed in by the material of the support structure 105 before being absorbed by the top permeable layer 201 lying underneath the support structure 105. Thus, the portion 603 of the urine 601 present in the support structure 105 and the urine 601, present in the gap between the electrodes 103a and 103b and the top permeable layer 201, can also form a closed electrical circuit that can result in an alert. When the portion 603 of the urine 601, present in the support structure 105 and the urine 601 present in the gap, get absorbed by the diaper 200, the electrical circuit breaks. Here also, the moisture 602 retained by the top permeable layer 201 will not be detected by the electrodes 103a and 103b due to the gap between the electrodes 103a and 103b, and the top permeable layer 201. Thus, the alerting device 400 will not generate false alerts based on the retained moisture 602 of the top permeable layer 201.

Figure 6E:
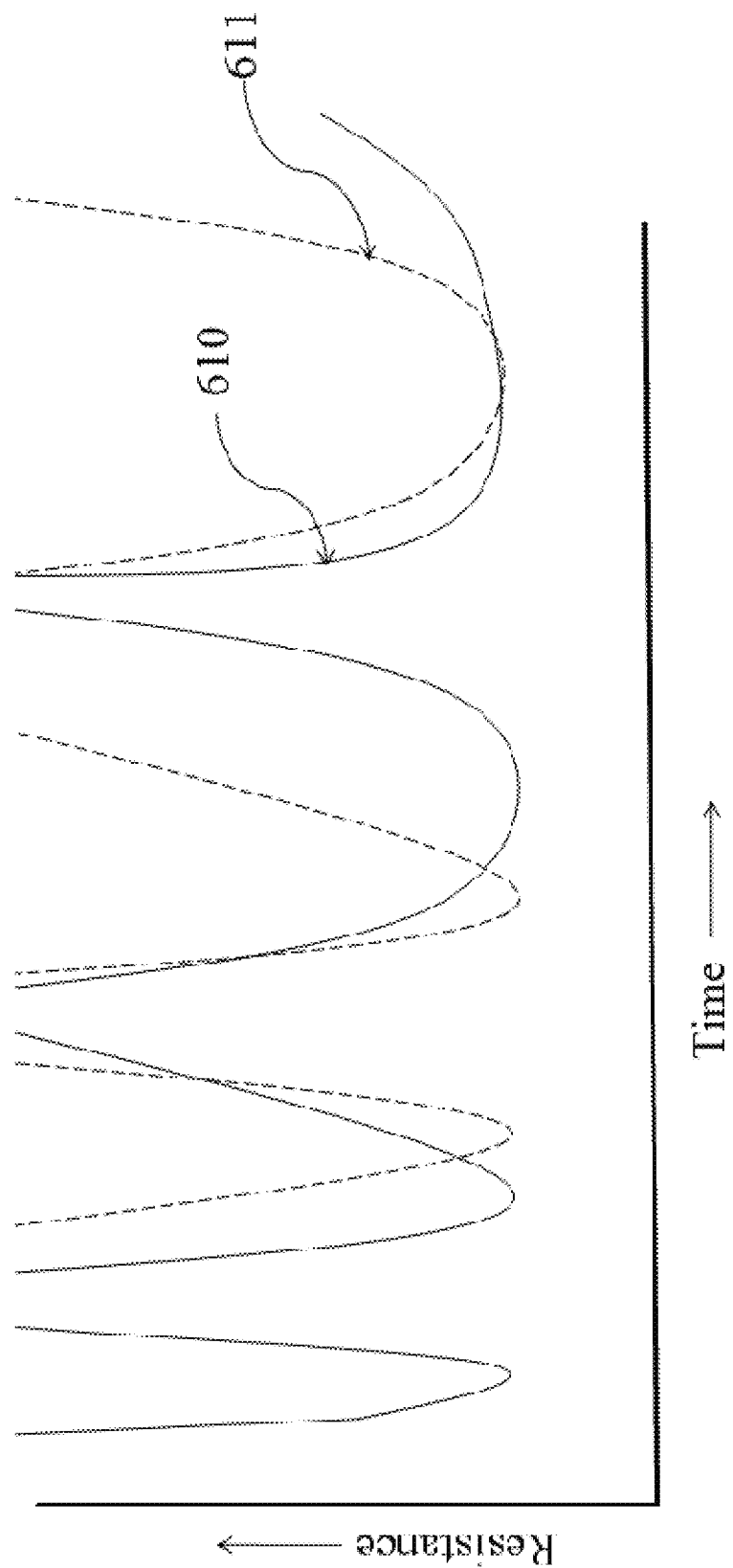
FIG. 6E is a graphical representation of the resistances detected by the alerting device when a wearer urinates inside the diaper over a course of time.

FIG. 6E illustrates a graphical depiction of resistance detected by the alerting device 400 when a user urinates in the diaper 200 having the sensor unit 100 and the support structure 105 as described in the previous embodiments. When the diaper is dry, there is no closed circuit and resistance can be considered as extremely high. When a user urinates, the urine will form a closed circuit between the electrodes 103a and 103b for duration of time required for the diaper 200 to absorb the urine. After, that there will again be a substantial open circuit between the electrodes 103a and 103b. The alerting device 400 can sense a decrease in resistance when the closed circuit is formed and an increase of resistance with subsequent formation of a substantial open circuit. When, the user urinates again, another closed circuit is formed and it also remains till the time the urine is not absorbed by the diaper 200. However, since the diaper is already wet, the rate of absorption of the urine will be relatively slower. The process repeats every time a wearer urinates in the diaper 200, till the time the diaper is completely saturated and cannot absorb any more urine. Then, the closed circuit formed will remain nearly constant. The changes of resistance detected by the alerting device 400 are shown by the graph trace 610. The resistance information can be used by the alerting device 400 to generate alerts at different intervals indicating different saturation level of the diaper. The amount of time a closed circuit remains can also be used to identify volume of urine excreted by the wearer. Also, with subsequent urination, urine gets spread to other portions of the diaper 200 and as a result newer closed circuits are formed. The resistance of the new closed circuits are depicted using graph trace 611. The resistance of the newer closed circuits will also decrease and increase in a similar way as that of the existing closed circuit. Only the rate of increase in resistance in newer closed circuits will vary based on the saturation level of that portion of the diaper 200. Also, as evident from FIG. 6E, graph traces of resistances forms a U-shaped curves. Area under the curve can also be used to calculate the volume of urine excreted by the user. Hence, by tracking down how many closed circuits are formed and rate of decrease of resistance in those closed circuits, overall saturation level of the diaper 200 can be ascertained. Thus, using the support structure 105, the time required to determine saturation level of a diaper is reduced.

In a further embodiment, the sensor strip 101, along with the support structure 105, can be used to detect number of times a wearer has excreted. As explained in previous embodiments, the sensor strip 101 detects presence of urine for duration of time till the urine is not being absorbed by inner absorbent layers of a diaper, and then it stops detecting the moisture retained by the top permeable layer of the diaper. When a wearer excretes again, the sensor strip 101 detects the presence of urine again for duration of time till the urine is not being absorbed by the inner absorbent layers of the diaper. Thus, the sensor strip 101 can be used to count the number of times a wearer has urinated. This can be used to track health condition of the wearer.

The sensor strip 101 and the alerting device 400, when used in diaper 200 designed for adult females or babies, who have a tendency to urinate in small amount from time to time, does not generate a long continuous alert every time a small amount of urine is excreted. When the diaper 200 has absorbed in large amount of urine, its absorption process will get slower, and then the excreted urine will be in touch with the electrodes 106 for a longer duration of time. Thus, a continuous alert for a longer duration of time will be generated by the alerting device 400 to indicate that excreted urine is taking longer time to be absorbed inside the diaper 200. This alert can also indicate that the diaper 200 has reached saturation.

Figure 7A:
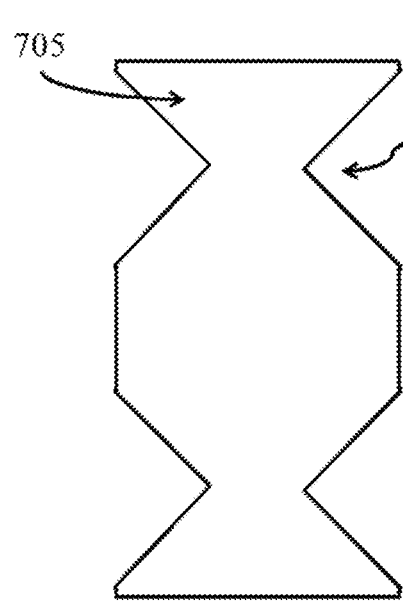
FIG. 7A-7C are the plan views of the various designs of the support structure and corresponding slots.
Figure 7B:
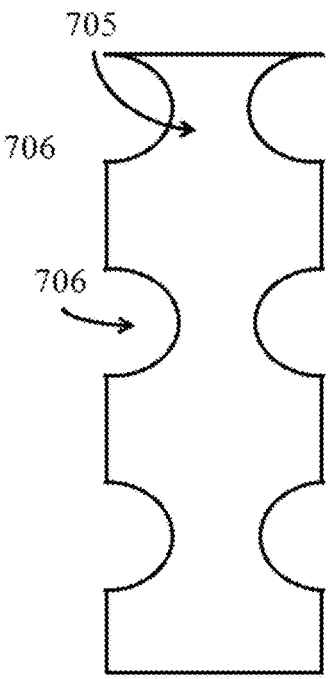
Figure 7C:
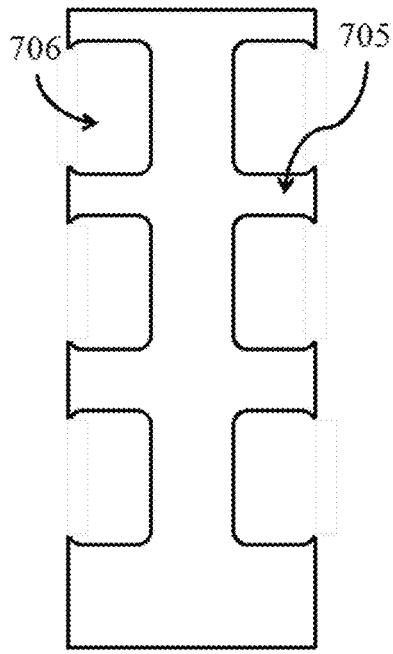

In accordance with the present invention, as shown in FIG. 7A-7C, the slots that are made on the support structure 705 can be of any shape and design. The thickness of the support structure 705 and slots 706 are cut in such a way that there is a uniform gap between electrodes of a sensor strip and a top permeable layer of a diaper. The gap is large enough not to cause capillary action. The design and the number of slots 706 will be directly related to the number of electrodes that are present on a sensor strip. The slots 706 are made in places that expose electrodes present on a sensor strip towards the top permeable layer of a diaper. Having multiple electrodes at different places within a sensor strip allows detection of urine at multiple locations. The more the number of electrodes spaced apart along the length of a sensor strip, more precise location of urine excretion can be detected. Hence, it is a trade off between the cost of printing electrodes on a sensor strip and precision of location detection of urine on a diaper. It can be understood that any person skilled in the art can decide upon the number of electrodes that can be present in a sensor strip and choose a support structure and corresponding slot design and number of slots accordingly.

In another aspect of the invention, the support structure is not made of a continuous block of foam rubber or similar materials, but made up of discrete portions with slots cut out on them and spread across the entire length of a sensor strip.

Figure 8:
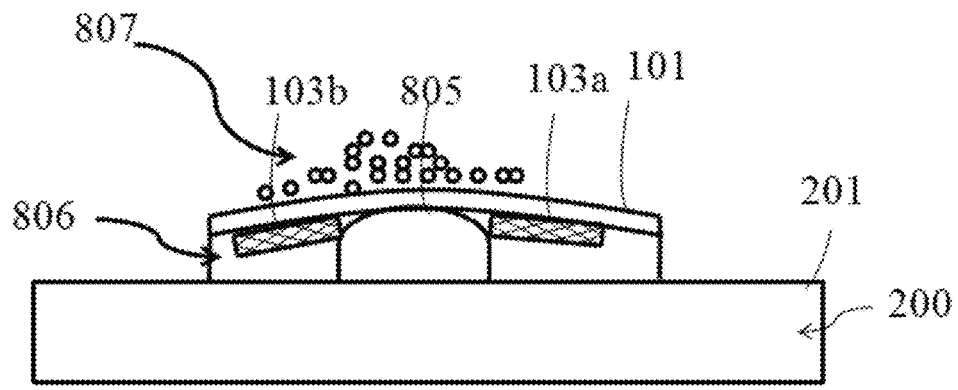
FIG. 8 is a cross sectional view of the sensor strip with a varying thickness support structure as per one of the embodiment.

In another aspect of the invention, as shown in FIG. 8, support structure 805 is designed in such a way that the thickness of the support structure 805 is more near a central region and less near edge regions. The sensor strip 101 with electrodes 1103a and 103b printed on the bottom surface of the same are attached on top of the support structure 805. The sensor strip 101 and the supports structure 805 are placed on top of the top permeable layer 201 of the ordinary diaper 200, such that the supports structure along with its slots 806 causes a non-capillary gap between the top permeable layer 201 and the electrodes 103a and 103b. Having such a design of support structure 805 allows the sensor strip 101 to form a small elevated portion at its central region that allows urine or other body fluids 807 to move faster towards the top permeable layer 201 of the diaper 200. Thus, such a structure causes a fast detection of urine in a diaper. In this structure also, the thickness of the central region and the thickness near the edge regions of the support structure 805 needs to maintained such that the gap between the electrodes 103a and 103b and the top permeable layer 201 of a diaper 200, be sufficient enough not to cause capillary action. It must also be noted the small elevated portion of the sensor strip 101 is not too steep, so as not to cause discomfort to a wearer of the diaper.

Figure 9:
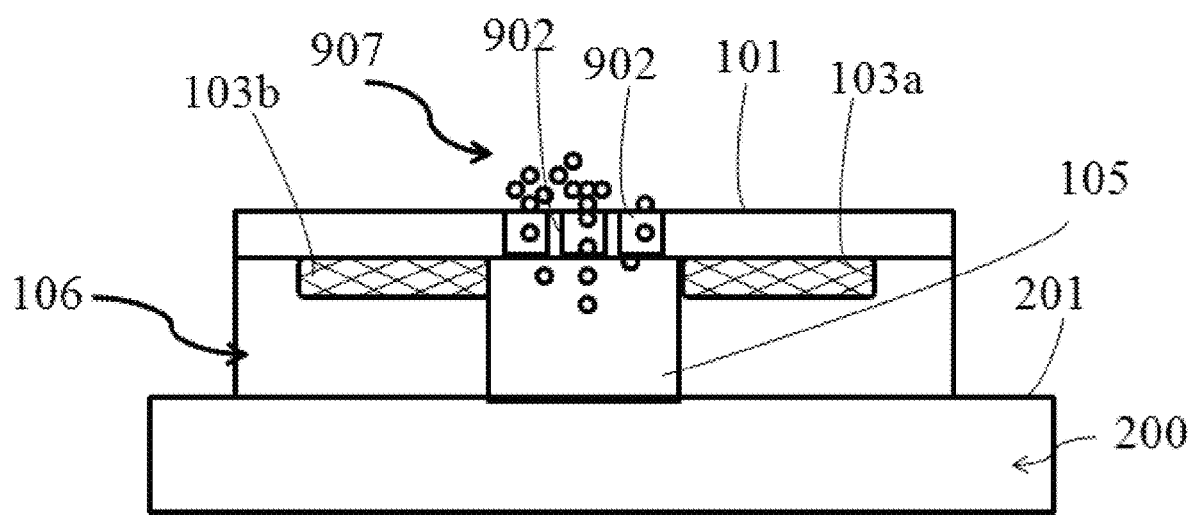
FIG. 9 is a cross sectional view of a sensor strip with pores in the sensor strip as per one of the embodiment.

In yet another embodiment of the invention, as shown in FIG. 9, small pores 902 are made in the plastic or hydrophobic layer of the sensor strip 101, in places not overlapping the electrodes 103a and 103b. The pores 902 are made to allow transfer of urine or body fluids 907 from the top of the plastic or hydrophobic layer of the sensor strip 101 to the support structure 105 and then from the support structure 105 to the diaper 200. Having pores 902 at predetermined places allows quick transfer of urine or body fluids from top of the sensor strip 101 to the diaper 200, and doesn't allow urine to accumulate over the sensor strip 101.

It will now be readily appreciated that the present invention may be used to advantageously sense wet conditions on items other than diapers, including, without limitation, surgical dressings, bed coverings, clothing, skin, etc. Also, it should now be understood that body fluids of all types can be sensed, initiating the signal produced by the invention, including, without limitation, urine, blood, saliva, sweat, vomits, mucus, semen, tears, milk and feces, and water, all of which are electrolytic in varying degrees.

It is also contemplated to be within the scope of our invention that the pores on the sensor strip, design and number of the slots on support structure, the thickness and design of the support structure can all be combined in parts or in whole in designing a sensor unit, where the electrodes and absorbent layer of diaper is maintained at a gap from each other.

The invention may be used for a variety of applications. In addition to quickly alerting a caretaker that a wearer of a diaper within their care has excreted a body fluid, the device may be used in conjunction with urine receptacles positioned within the diapers for catching urine for analysis. It is frequently desirable to perform bacterial analysis, such as a bacteria count, on such collected samples, and the results may be skewed if the urine sits for long periods and the bacteria multiply. It can also be used to identify the number of times a wearer is excreting urine that could help identify other health conditions like diabetes.

The invention claimed is:

1. A method of identifying saturation level of a diaper, the method comprising steps of:
   tracking resistance formed between plurality of electrodes due to urine over a period of time;
      wherein the resistance decreases when the urine is excreted; and
      wherein the resistance increases when the urine starts getting absorbed inside the diaper;
   calculating rate of increase of the resistance; and
   determining when the diaper is saturated based on the rate of increase of the resistance, after urination events.

2. A method as in claim 1, wherein the rate of increase of the resistance is calculated over a predetermined duration of time.

3. A method as in claim 1, wherein the saturation of the diaper is determined by where multiple areas of the diaper exhibit a higher level than predefined level of saturation.

4. A method as in claim 1, wherein the method further comprises steps of:
   identifying resistances of plurality of the closed circuits formed between the plurality of electrodes due to urine;
   tracking the resistances;
   calculating rates of increase of the resistances after every urination event over a period of time; and
   determining the diaper is saturated when rates of increase of the resistances of at least two of the plurality of the closed circuits are less than a predetermined threshold.

5. A method as in claim 4, wherein the predetermined threshold is dynamically selected for each of the plurality of closed circuits.

6. A method of determining when a diaper is saturated, the method comprising steps of:
   tracking resistances of closed circuits formed between plurality of electrodes due to urine;

calculating rates of rise of the resistances of the closed circuits after urination event; and determining the diaper is saturated when the rates of rise of the resistances of at least two of the closed circuits, are less than a threshold after a predetermined duration of time.

7. A method as in claim 6, wherein the urination event is a time duration between which resistances of the closed circuits decreases rapidly.

8. A method as in claim 6, wherein the threshold is dynamically selected for each of the closed circuits individually.

9. A method of detecting saturation level of a diaper, the method comprising steps of: tracking resistances of plurality closed circuits formed between plurality of electrodes due to body fluids; identifying at least a closed circuit as a saturated closed circuit when its corresponding resistance is at a substantial minimum value; comparing resistances of other closed circuits with the resistance of the saturated closed circuit; and determining when the diaper is saturated based on rate of increase of total resistance of the plurality of closed circuits, other than the saturated closed circuit, is less than a percentage threshold of the resistance of the saturated closed circuit.

10. A method as in claim 9, wherein identifying at least a closed circuit as a saturated closed circuit comprises steps:
tracking decrease and increase of resistance of the closed circuit over a period of time; and
determining the closed circuit is saturated when the rise of resistance of the closed circuit over a period of time is less than a threshold.

11. A method of sensing body fluid in an absorbent article, the method comprising steps of: placing a sensor strip comprising of plurality of conducting elements on the absorbent article, wherein there is a gap between the conducting elements and the absorbent article; forming an electrical closed circuit between the conducting elements when the body fluid is present on the absorbent article; and based on rate of increase of resistance, tracking the resistance of the electrical closed circuit.

12. A method as in claim 11, wherein the gap is large enough to prevent capillary action of the body fluid in the gap.

13. A method as in claim 11, wherein a support structure is placed between the sensor strip and the absorbent article.

14. A method as in claim 13, wherein the support structure has multiple slots.

15. A method as in claim 14, wherein the multiple slots expose the conducting elements towards an absorbent article.

16. A sensor unit to be used with a moisture detection and alerting system, comprising: at least two electrodes configured on a sensor strip; a support structure attached to said sensor strip to cover said electrodes; wherein said support structure having multiple slots cut out to expose individually each electrode at multiple places to a diaper to detect moisture at various location of the diaper and based on rate of increase of resistance, determine when the diaper is saturated.

17. The sensor unit as in claim 16, wherein said sensor unit is placed on a wearer side of an ordinary diaper.

18. The sensor unit as in claim 17, wherein the at least one slot exposes the at least one electrode to the diaper to detect moisture.

19. The sensor unit as in claim 18, wherein the support structure causes a gap between the at least one electrode and the diaper.

20. The sensor unit as in claim 16 is electrically coupled to an alerting device.

21. The sensor unit as in claim 16, wherein the support structure is thick enough to prevent capillary action between the at least one electrode and the diaper.

22. The sensor unit as in claim 21 wherein:
the at least one electrode detects body fluid for a duration of time before the body fluid is being absorbed by a diaper.

23. The sensor unit as in claim 21 wherein:
the sensor unit detects the excretion of body fluid for multiple times before the diaper is disposed.

* * * * *